(12) United States Patent
Tornier

(10) Patent No.: US 6,454,809 B1
(45) Date of Patent: Sep. 24, 2002

(54) MODULAR ACETABULAR OR COTYLOID IMPLANT

(75) Inventor: Alain Tornier, Saint-Ismier (FR)

(73) Assignee: Tornier SA, Saint-Ismier (FR)

( * ) Notice: Subject to any disclaimer, the term of this patent is extended or adjusted under 35 U.S.C. 154(b) by 0 days.

(21) Appl. No.: 09/622,901

(22) PCT Filed: Mar. 2, 1999

(86) PCT No.: PCT/FR99/00459

§ 371 (c)(1),
(2), (4) Date: Nov. 1, 2000

(87) PCT Pub. No.: WO99/44545

PCT Pub. Date: Sep. 10, 1999

(30) Foreign Application Priority Data

Mar. 3, 1998 (FR) .............................................. 98 02795

(51) Int. Cl.⁷ .................................................. A61F 2/34
(52) U.S. Cl. .................................. 623/22.32; 623/22.38
(58) Field of Search ........................... 623/22.21, 22.23, 623/22.31, 22.32, 22.34, 22.35, 22.36, 22.37, 22.38

(56) References Cited

U.S. PATENT DOCUMENTS

| 4,596,580 A | 6/1986 | Weill |
| 4,681,589 A | 7/1987 | Tronzo |
| 4,743,262 A | 5/1988 | Tronzo |
| 5,326,368 A | 7/1994 | Collazo |
| 5,480,448 A | 1/1996 | Mikhail |
| 5,549,692 A | 8/1996 | Hauser et al. |
| 5,549,701 A | 8/1996 | Mikhail |

FOREIGN PATENT DOCUMENTS

| DE | 4126837 | 11/1992 |
| EP | 0142759 | 5/1985 |
| EP | 0551794 | 7/1993 |
| FR | 2578162 | 9/1986 |
| FR | 2651996 | 3/1991 |
| FR | 2703583 | 10/1994 |
| FR | 2748656 | 11/1997 |
| GB | 2159416 | 12/1985 |
| WO | 93/08770 | 5/1993 |
| WO | 95/15734 | 6/1995 |
| WO | 97/16137 | 5/1997 |

*Primary Examiner*—David J Isabella
(74) *Attorney, Agent, or Firm*—Greenblum & Bernstein, P.L.C.

(57) ABSTRACT

An acetabular or cotyloid implant. The implant includes a cotyle having an internal cavity which is adapted to receive an insert. At least one groove is arranged on an outer surface of the cotyle. The at least one groove is adapted to receive an independent element.

36 Claims, 7 Drawing Sheets

FGIURE 5b

MODULAR ACETABULAR OR COTYLOID IMPLANT

BACKGROUND OF THE INVENTION

1. Field of the Invention

The present invention relates to a modular acetabular or cotyloid implant adapted to be positioned in a damaged articular cavity to cooperate especially with the head of a femoral prosthesis, the assembly constituting a total hip prosthesis.

2. Description of Background and Relevant Information

Acetabular implants made entirely of plastic material, such as polyethylene, are known, they are adapted to cooperate with a natural or artificial femoral head in a hip arthroplasty. Such implants are positioned by using a cement that affixes them to the damaged bone cavity.

Acetabular implants comprising a metallic cotyle and a plastic insert that is housed in the internal cavity of the cotyle are also known. The latter can be fixed within the human cotyle of a patient either by means of cement, or directly by means of screws that penetrate into the hip bone.

When the implant is cemented or screwed into the human cotyle of a patient, the outer wall of the metallic cotyle is either coated with a thickness of hydroxyapatite, or provided with a rough surface to enable bone regeneration and, therefore, the fixing of the implant.

A screw type acetabular implant comprises a metallic cotyle that is bored along its periphery with a certain number of holes providing the surgeon with a plurality of solutions for positioning the fixing screws.

In the case where the bone cotyloid cavity is destroyed, it is impossible to set an implant of the conventional type such as described hereinabove.

Summary of the Invention

The acetabular or cotyloid implant according to the present invention is of the modular type and makes it possible, when the bone cotyloid cavity is substantially destroyed, to locate the original anatomical markers and to ensure instant stability by solid supports and anchors.

Moreover, a bone stock is provided to be introduced by grafting, in order to fill the spaces left between the implant according to the present invention and the healthy bone.

The modular acetabular or cotyloid implant according to the present invention includes a metallic cotyle receiving a plastic insert in an internal cavity, the cotyle comprising, on its outer surface, grooves that are arranged starting from its peripheral edge toward the pole so as to enable the fixing of various independent elements allowing to locate the original anatomical markers of the articulation and to ensure instant stability by solid supports and anchors.

The acetabular or cotyloid implant according to the invention includes, on the outer surface of the metallic cotyle, grooves which each have a conical profile, the largest end of which is turned toward the pole, whereas the other, smaller end, is directed close to the peripheral edge to avoid the ejection of the independent elements during the insertion of the metallic cotyle in the acetabular cavity.

The acetabular or cotyloid implant includes grooves having a dovetail conical profile.

The acetabular or cotyloid implant includes grooves each having a T-shaped profile whose upper and opposite edges are inclined with respect to the axis of the groove, such that the largest end is turned toward the pole of the metallic cotyle, whereas the lower and opposite edges of the T are parallel with respect to one another.

The acetabular or cotyloid implant includes grooves each having a T-shaped profile whose lower and opposite edges are inclined with respect to the axis of the groove, such that the largest end is turned toward the pole of the metallic cotyle, whereas the upper and opposite edges of the T are parallel with respect to one another.

The acetabular or cotyloid implant includes grooves each having a T-shaped profile whose upper and lower edges are inclined with respect to the axis of the groove, such that the largest end is turned toward the pole of the metallic cotyle.

The acetabular or cotyloid implant according to the present invention includes, on the outer surface of the metallic cotyle, grooves that open up at the level of the peripheral edge.

Furthermore, the present invention also relates to a metallic cotyle for an acetabular or cotyloid implant comprising, on its outer surfaces, grooves that are arranged starting from its peripheral edge toward the pole to enable the fixing of various independent elements, such as fixing plates or filling wedges, so as to position and immobilize the cotyle according to the original anatomical markers.

The metallic cotyle according to the present invention comprises grooves which each have a conical profile, the largest end of which is turned toward the pole, whereas the other, smallest end is directed close to the peripheral edge to prevent the ejection of the independent elements during the insertion of the metallic cotyle in the acetabular cavity.

The metallic cotyle for an acetabular or cotyloid implant includes grooves with a dovetail conical shape on its outer surface.

The metallic cotyle according to the present invention includes, on its outer surface, grooves each having a T-shaped profile whose upper and opposite edges are inclined with respect to the axis of the groove, such that the largest end is turned toward the pole of the metallic cotyle, whereas the lower and opposite edges of the T are parallel with respect to one another.

The metallic cotyle according to the invention includes, on its outer surface, grooves each having a T-shaped profile whose lower and opposite edges are inclined with respect to the axis of the groove, such that the largest end is turned toward the pole of the metallic cotyle, whereas the upper and opposite edges of the T are parallel with respect to one another.

The metallic cotyle for an acetabular or cotyloid implant includes, on its outer surface, grooves each having a T-shaped profile whose upper and lower edges are inclined with respect to the axis of the groove, such that the largest end is turned toward the pole of the metallic cotyle.

The metallic cotyle according to the present invention includes on its outer surface, grooves that open up on the side of the peripheral edge.

BRIEF DESCRIPTION OF THE DRAWINGS

The description that follows, with reference to the annexed drawings provided by way of non-limiting examples, will make it possible to better understand the invention, its characteristics, and the advantages which it can provide:

FIGS. 5a and 5b are views showing a first variation of the conical profile of the grooves receiving the independent elements.

DETAILED DESCRIPTION OF THE INVENTION

Figure 1:
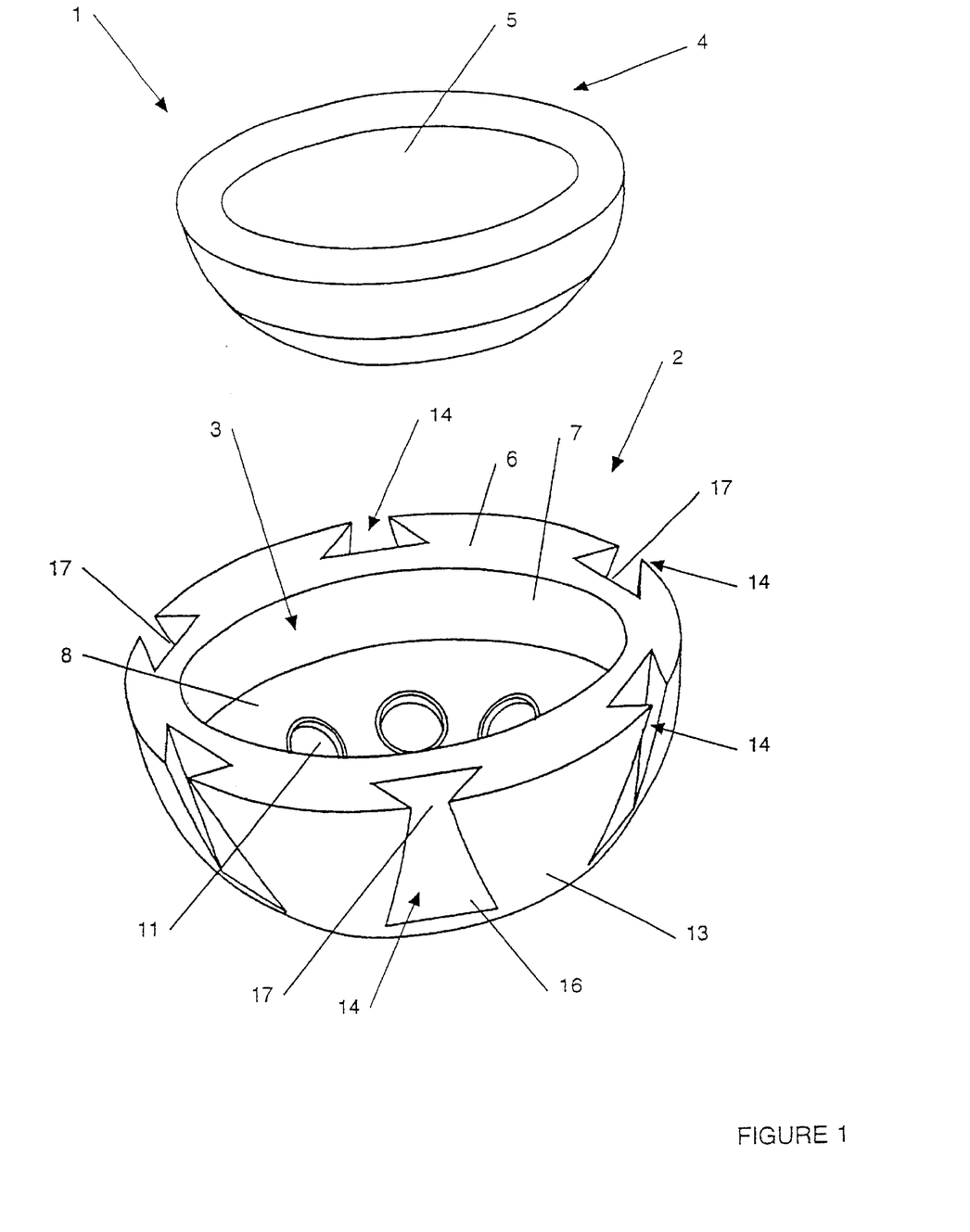
FIG. 1 is a perspective view showing the metallic cotyle and the insert of the acetabular or cotyloid implant according the present invention.
Figure 2:
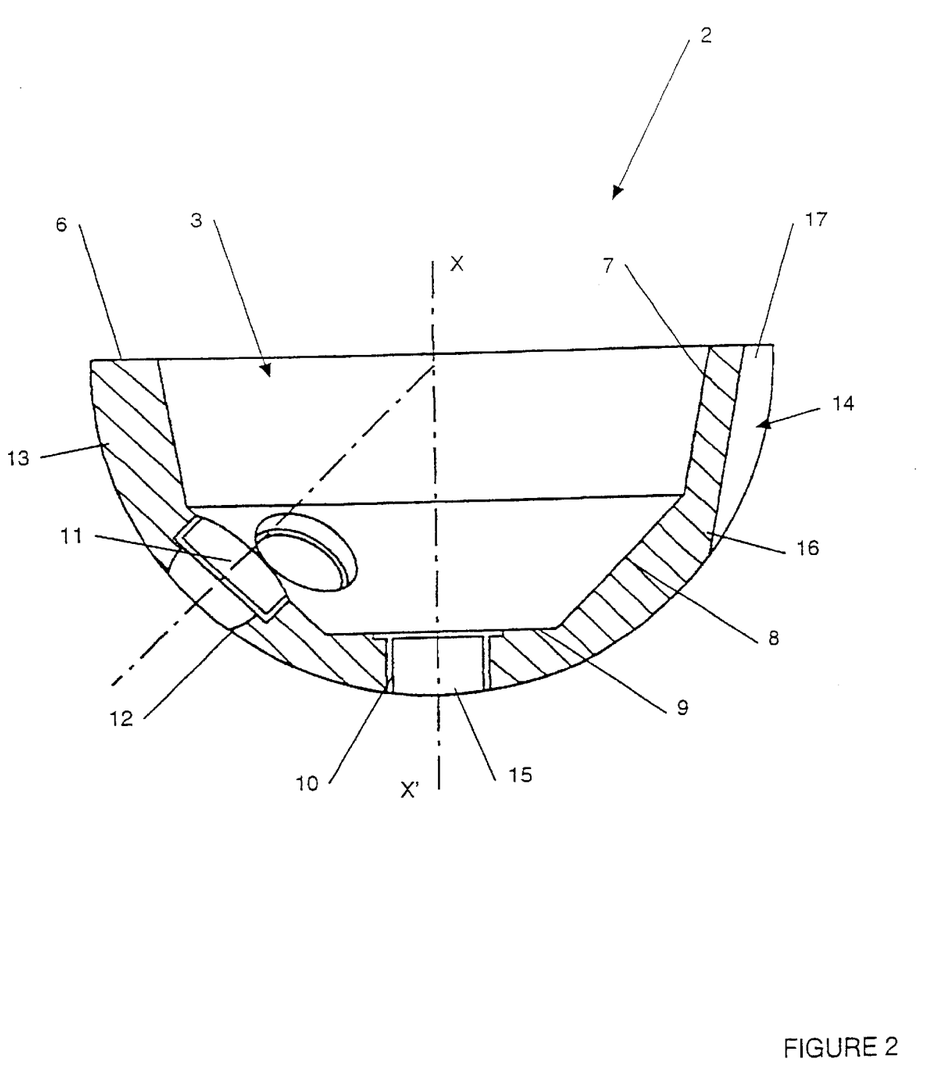
FIG. 2 is a cross-section showing the metallic cotyle of the acetabular or cotyloid implant without the independent elements.

An acetabular or cotyloid implant 1 is shown in FIGS. 1 and 2, which comprises a metallic cotyle 2 provided with an internal cavity 3 in which is engaged a plastic insert 4 adapted, for example, to receive in its housing 5 a ball of a femoral implant, not shown.

The metallic cotyle 2 has a hemispherical outer profile adapted to being fixed in the acetabular cavity A of the hip bone C (see FIGS. 8–11) which can be previously arranged depending on the bone condition.

The metallic cotyle 2 can be made of stainless steel or titanium alloy, or of any other biocompatible material.

The insert 4 adapted to receive the ball of a femoral implant can be made of a biocompatible plastic material such as high-density polyethylene or ceramic.

The metallic cotyle 2 comprises a peripheral edge 6 demarcating the inlet of the internal cavity 3. For example, the latter has, perpendicular to the peripheral edge 6, a first slightly conical portion 7 which is extended by another portion 8 having a substantially conical profile.

The cone-shaped portion 8 is ended by a flat bottom 9 that is bored in its center with a through hole 10 comprising a threaded portion. The through hole 10 is carried by the vertical axis XX' passing by the pole 15 of the cotyle 2.

It is understood that the internal profile of the cavity 3 can be different without modifying the object of the present invention.

The peripheral edge 6 can be affixed, in a known manner, to lugs, not shown, which are uniformly distributed over the circumference of the metallic cotyle 2 to enable the angular indexing of the plastic insert 4 with respect to the cotyle 2.

The internal cavity 3 is bored with a plurality of through holes 11 enabling the positioning of fixing screws not shown. In our example, the holes 11 are pierced along a same radius arranged in the cone-shaped portion 8 of the internal cavity 3. The metallic cotyle 2 can comprise a greater number of holes 11 distributed along different radii.

Each hole 11 comprises a housing 12 with a substantially conical or hollow profile making it possible to adjust the angular position of the axis of the fixing screw and to receive the outer profile of its head, so that the latter is the farthest away possible from the cavity 3 so as not to come in contact with the plastic insert 4.

The metallic cotyle 2 comprises an outer surface 13 that has grooves 14 with identical profiles uniformly distributed over the circumference of the cotyle for fixing independent elements 26, 27, 28, 29, and 30 shown in FIGS. 3a–3e.

Each groove 14 is arranged on an axis or longitude passing by the pole 15 of the metallic cotyle 2. Indeed, each groove 14 extends from the peripheral edge 6 toward the pole 15 of the cotyle 2.

The grooves 14 each have a conical profile, the largest end 16 of which is turned toward the pole 15, whereas the other, smallest end 17 is directed close to the peripheral edge 6.

Figure 4A:
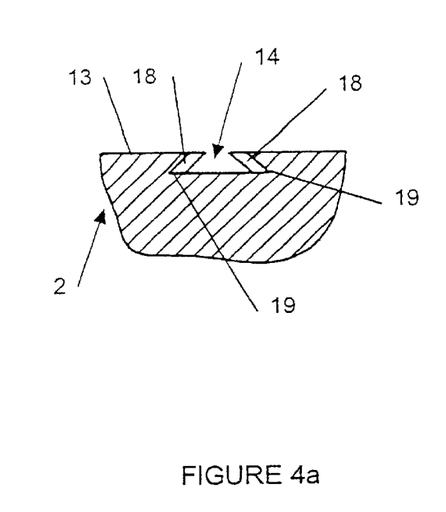
FIGS. 4a and 4b are views showing the dovetail conical profile of the grooves provided on the outer surface of the metallic cotyle for fixing the independent elements.
Figure 4B:
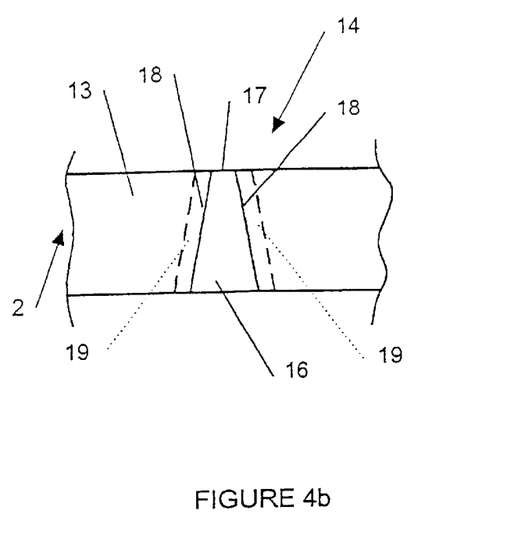

FIGS. 4a and 4b show a partial cross-section of the metallic cotyle 2 that comprises, on its outer surface 13, grooves 14 with a dovetail conical profile whose upper 18 and lower 19 opposite edges are inclined such that the largest end 16 is turned toward the pole 15.

Figure 5A:
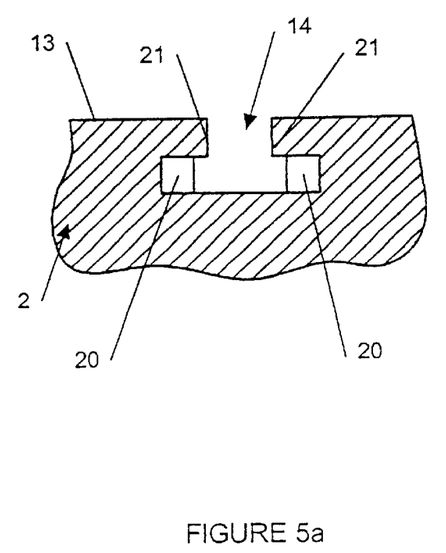

FIGS. 5a and 5b show a first variation of the conical profile of the grooves 14 provided on the outer surface 13 of the metallic cotyle 2.

Each groove 14 has a T-shaped profile whose lower and opposite edges 20 are inclined with respect to the axis of the groove, such that the largest end 16 is turned toward the pole 15 of the metallic cotyle 2, whereas the upper and opposite edges 21 of the T are parallel with respect to one another.

Figure 6A:
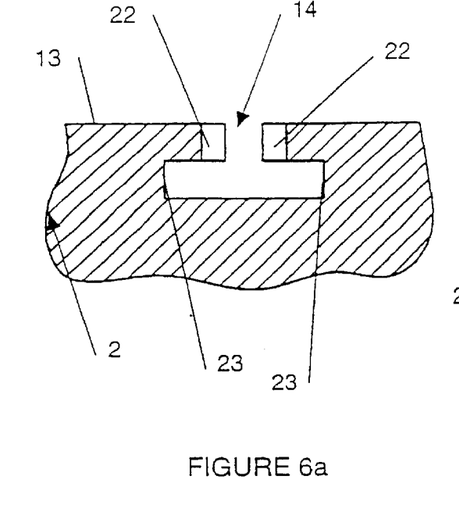
FIGS. 6a and 6b are views showing a second variation of the conical profile of the grooves receiving the independent elements.
Figure 6B:
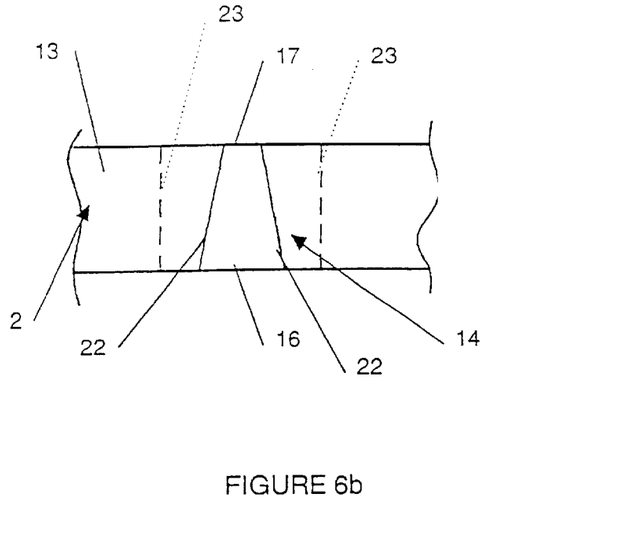

FIGS. 6a and 6b show a second variation of the conical profile of the grooves 14 provided on the outer surface 13 of the metallic cotyle 2.

Each groove 14 has a T-shaped profile whose upper and opposite edges 22 are inclined with respect to the axis of the groove, such that the largest end 16 is turned toward the pole 15 of the metallic cotyle 2, whereas the lower and opposite edges 23 of the T are parallel with respect to one another.

Figure 7A:
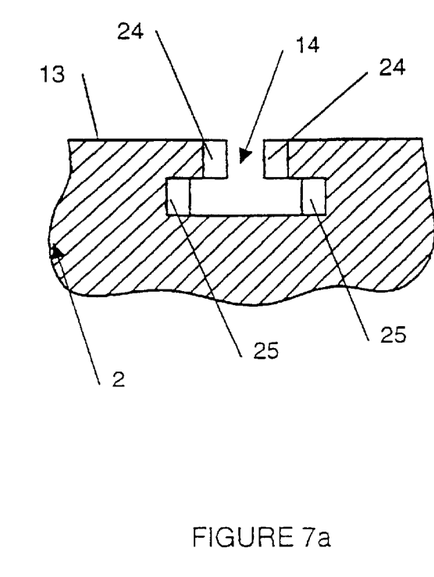
FIG. 7a and 7b are views showing a third variation of the conical profile of the grooves receiving the independent elements.
Figure 7B:
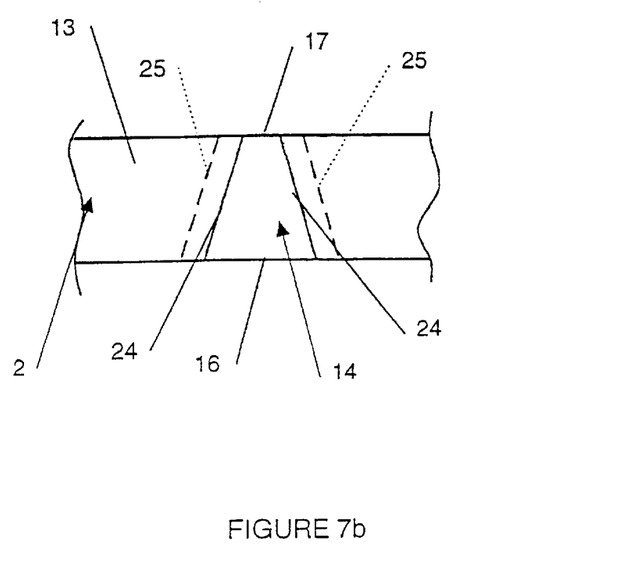

FIGS. 7a and 7b show a third variation of the conical profile of the grooves 14 provided on the outer surface 13 of the metallic cotyle 2.

Each groove 14 has a T-shaped profile whose upper 24 and lower 25 edges are inclined with respect to the axis of the groove, such that the largest end 16 is turned toward the pole 15 of the metallic cotyle 2.

It is noted that for each variation of the profile of the groove 14, the largest end 16 is turned toward the pole 15, necessarily positioning the other, smallest end 17 on the side of the peripheral edge 6 of the metallic cotyle 2.

The metallic cotyle 2 can also comprise, on its outer surface 13, grooves 14 with a conical profile which do or do not open up on the side of its peripheral edge 6. The profile of the grooves 14 may or may not be conical, so long as it enables the independent elements 26, 27, 28, 29, and 30 to be wedged on the outer surface 13 of the metallic cotyle 2.

Figure 3A:
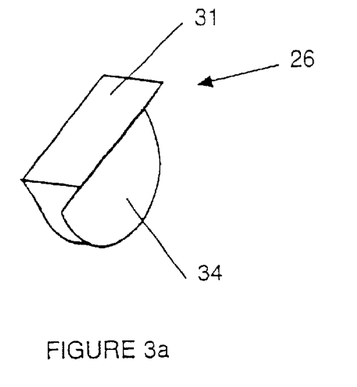
FIGS. 3a–3e are perspective views showing the independent elements which get fixed on the outer surface of the metallic cotyle.
Figure 3B:
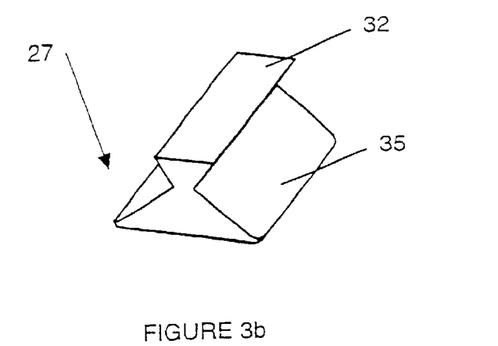
Figure 3C:
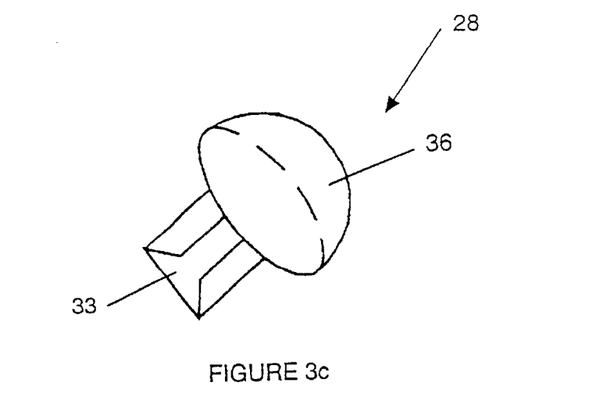

FIGS. 3a–3c show the independent elements 26, 27, and 28 forming wedges when the acetabular cavity A of the hip bone C is destroyed, and it is necessary to locate stable supports for positioning the metallic cotyle 2.

The elements 26–28 comprise a tenon 31, 32, and 33, respectively, having an outer profile that is complementary to that of the grooves 14. The profile of each tenon depends upon that which the corresponding groove 14 is going to have, as a function of the solutions described hereinabove, in order to be capable of wedging the elements 26–28 on the outer surface 13 of the metallic cotyle 2.

The tenon 31 of the element 26 is affixed to a disc 34 in the form of a half-circle that is parallel to the longitudinal axis of the tenon. The dimensions of the disc 34 can vary according to the space E of the acetabular cavity A to be filled.

The tenon 32 of the element 27 is overlaid by a triangle-shaped piece 35 the largest base of which is opposite the tenon. The dimensions of the piece 35 can vary according to the space E of the acetabular cavity A to be filled.

The tenon 33 of the element 28 is affixed to a shell 36 in the form of a half-sphere that is arranged at a certain distance from the tenon. The dimensions of the shell 36 can vary according to the space E of the acetabular cavity A to be filled.

Figure 3D:
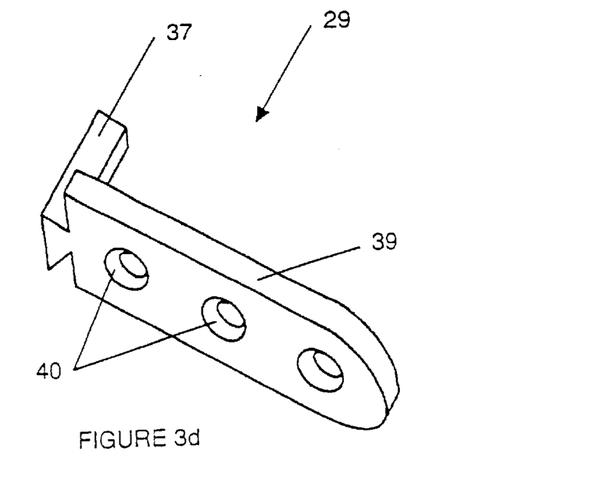
Figure 3E:
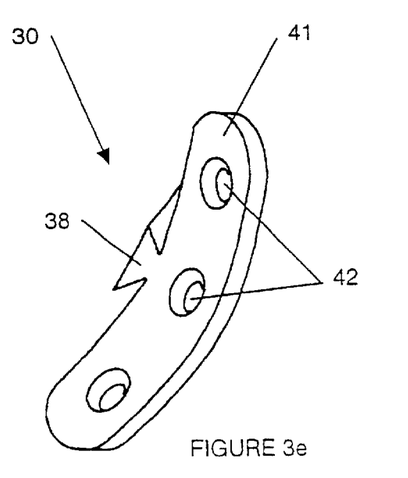

FIGS. 3d and 3e show two other independent elements 29 and 30 enabling the metallic cotyle 2 to be fixed against the hip bone C when the screws extending through the holes 11 are not sufficient for stabilizing the implant 1 in the acetabular cavity A.

The elements 29 and 30 comprise a tenon 37 and 38, respectively, cooperating with the corresponding groove 14 of the cotyle 2. The outer profile of each tenon 37, 38 is complementary to that of the groove 14 of the cotyle 2.

The tenon 37 of the independent element 29 is affixed, at one of its ends, to a rectilinear plate 39 bored with holes 40 for the passage of the fixing screws in the hip bone C. The plate 39 is arranged perpendicular to the tenon 37 of the element 29 (FIG. 3d).

The tenon 38 of the independent element 30 is affixed, at one of its ends, to a plate 41 having a curved profile and bored with holes 42 for the passage of the fixing screws in the hip bone C. The plate 41 cooperates in its center with the tenon 37, so that the curved profile extends at equal distance on both sides of the tenon.

Figure 8:
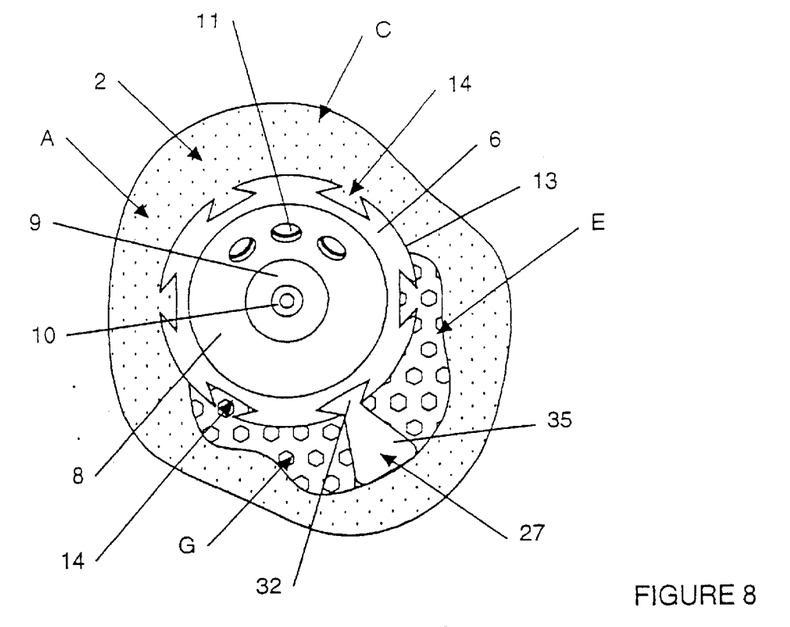
FIG. 8 is a top view showing the metallic cotyle within the acetabular cavity of the hip bone provided, for example, with the independent element of FIGS. 3a or 3b.
Figure 9:
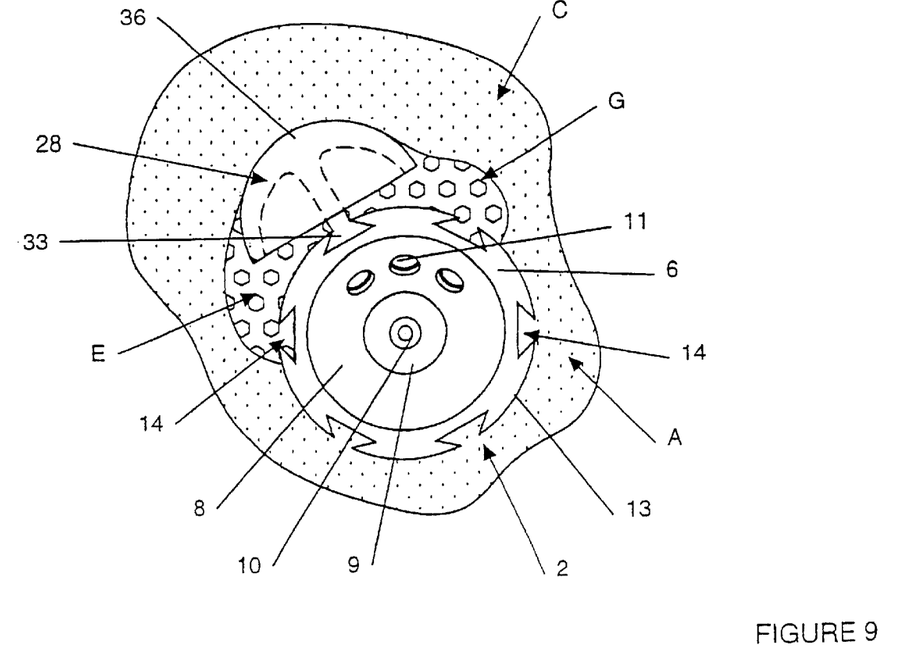
FIG. 9 is a top view showing the metallic cotyle within the acetabular cavity of the hip bone provided, for example, with the independent element of FIG. 3c.

FIGS. 8 and 9 show the positioning of the metallic cotyle 2 within the acetabular cavity A of the hip bone C, and a bone portion of which has been previously removed by the surgeon due to its deterioration.

Under these conditions, the surgeon fixes, in one or more grooves 14 of the outer surface of the cotyle 2, one or several of the elements 26, 27, and 28 forming the wedge, and more particularly that or those which will enable the best positioning possible of the cotyle 2 with respect to the original anatomical markers of the articulation.

Moreover, the surgeon fills the free space E, left between the outer surface 13 of the cotyle 2 and the healthy bone of the hip portion C, with a bone graft G to improve the stability and anchoring of the implant 1 over time.

The cotyle 2 is fixed to the bone either with or without the help of screws extending through the holes 11 in the known manner, or by way of one or several other elements 29, 30 previously anchored in the corresponding grooves 14.

The introduction of each independent element 26–30 into the corresponding groove 14 of the cotyle 2 occurs starting from the pole 15 toward the peripheral edge 6 until the tenon 31–38 is blocked in the groove.

The conical profile of each groove 14, the largest end 16 of which is turned toward the pole 15, whereas the other, smallest end 17 is directed close to the peripheral edge 6, makes it possible to avoid the ejection of the independent elements 26–30 during the insertion of said metallic cotyle 2 in the acetabular cavity A.

The cotyle 2 affixed to one or several independent elements 26, 27, and 28 forming a wedge constitutes, together with the plastic insert 4, an implant 1 called the recovery implant. The recovery implant 1 is used when the acetabular cavity A of the hip bone C is substantially damaged to locate the original anatomical markers and to ensure instant stability by solid supports and anchors.

Figure 10:
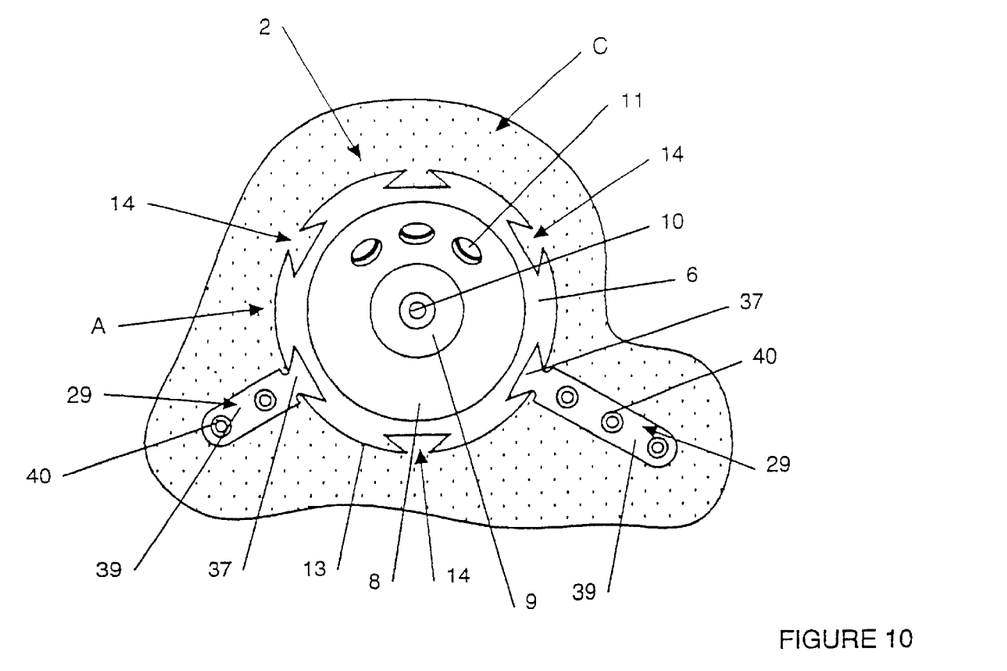
FIG. 10 is a top view showing the metallic cotyle within the acetabular cavity of the hip bone provided, for example, with the independent element of FIG. 3d.
Figure 11:
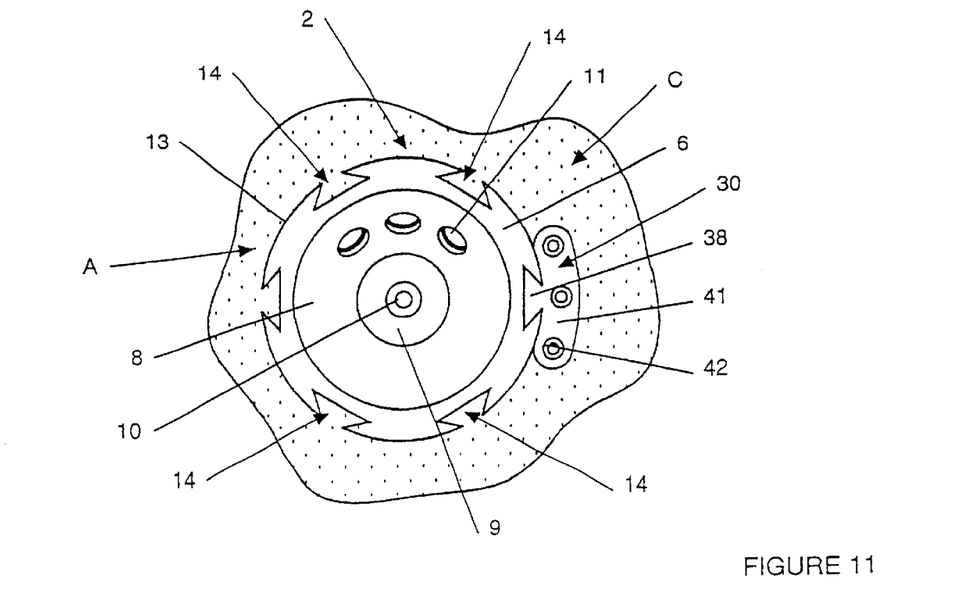
FIG. 11 is a top view showing the metallic cotyle within the acetabular cavity of the hip bone provided, for example, with the independent element of FIG. 3e.

FIGS. 10 and 11 show the positioning of the metallic cotyle 2 in the acetabular cavity A that does not comprise any substantial damage requiring the use of the independent elements 26–28. Thus, the implant 1 is used as a conventional implant.

The cotyle 2 can be fixed in the cavity A of the hip bone C directly by way of screws extending through the holes 11 provided in the cone portion 8 of the internal cavity 3.

In the case where the cotyle 2 is not satisfactorily stabilized, the surgeon can complete the anchoring by way of the elements 29 and 30. The latter are fixed on the outer surface 13 of the cotyle 2 by way of the grooves 14 as described previously.

Finally, the metallic cotyle 2 can be fixed in the cavity A only by the independent elements 29 and 30.

It is noted that the implant 1 according to the present invention is of the modular type since it can receive, on the outer surface 13 of the metallic cotyle 2, various independent elements 26–30 making it possible to constitute either a recovery implant, or a conventional implant, depending on the type of surgery.

What is claimed is:

1. An acetabular or cotyloid implant comprising a metallic cotyle receiving a plastic insert in an internal cavity, wherein the metallic cotyle comprises, on an outer surface, grooves arranged starting from a peripheral edge toward a pole to enable a fixing of various independent elements and making it possible to locate original anatomical markers of an articulation and to ensure instant stability by solid supports and anchors, and in that the grooves each have a conical profile, a largest end of which is turned toward the pole, whereas another, smaller end is directed toward the peripheral edge to avoid an ejection of the independent elements during insertion of the metallic cotyle in an acetabular cavity.

2. The acetabular or cotyloid implant according to claim 1, wherein the grooves each have a T-shaped profile whose upper and opposite edges are inclined with respect to an axis, such that the largest end is turned toward the pole of the metallic cotyle, whereas lower and opposite edges of the T are parallel with respect to one another.

3. The acetabular or cotyloid implant according to claim 1, wherein the grooves each have a T-shaped profile whose lower and opposite edges are inclined with respect to an axis, such that the largest end is turned toward the pole of the metallic cotyle, whereas upper and opposite edges of the T are parallel with respect to one another.

4. The acetabular or cotyloid implant according to claim 1, wherein the grooves each have a T-shaped profile whose upper and lower edges are inclined with respect to an axis, such that the largest end is turned toward the pole of the metallic cotyle.

5. The acetabular or cotyloid implant according to claim 1, wherein the outer surface of the metallic cotyle comprises grooves that open up toward the peripheral edge.

6. The acetabular or cotyloid implant according to claim 1, wherein the outer surface comprises grooves which have a dovetail conical profile.

7. The acetabular or cotyloid implant according to claim 1, wherein the independent elements comprise tenons, respectively, having a profile that is complementary to that of the grooves of the metallic cotyle.

8. The acetabular or cotyloid implant according to claim 7, wherein one tenon of an element is affixed to a disc in the form of a half-circle.

9. The acetabular or cotyloid implant according to claim 8, wherein the disc is parallel to a longitudinal axis of the tenon of the element.

10. The acetabular or cotyloid implant according to claim 7, wherein a tenon of an element is affixed to a triangle-shaped piece, a largest base of which is opposite the tenon.

11. The acetabular or cotyloid implant according to claim 7, wherein a tenon of an element is affixed to a shell in a form of a half-sphere.

12. The acetabular or cotyloid implant according to claim 7, wherein a tenon of an element is affixed to a rectilinear plate bored with holes for a passage of fixing screws in a hip bone.

13. The acetabular or cotyloid implant according to claim 12, wherein a plate is arranged perpendicular to the tenon of the element.

14. The acetabular or cotyloid implant according to claim 7, wherein a tenon of an element is affixed, at one end, to a curved plate that is bored with holes for a passage of fixing screws in a hip bone.

15. A metallic cotyle comprising an outer surface and grooves arranged starting from a peripheral edge toward a pole to enable fixing of various independent elements making it possible to locate original anatomical markers of an articulation and to ensure instant stability by solid supports and anchors, and in that the grooves each have a conical profile, the largest end of which is turned toward the pole, whereas another, smaller end is directed toward the peripheral edge to avoid an ejection of the independent elements during the insertion of the metallic cotyle in the acetabular cavity.

16. The metallic cotyle according to claim 15, wherein the outer surface comprises grooves that have a dovetail conical profile.

17. The metallic cotyle according to claim 15, wherein the grooves each have a T-shaped profile whose upper and opposite edges are inclined with respect to an axis, such that the largest end is turned toward the pole of said metallic cotyle, whereas lower and opposite edges of the T are parallel with respect to one another.

18. The metallic cotyle according to claim 15, wherein the grooves each have a T-shaped profile whose lower and opposite edges are inclined with respect to an axis, such that the largest end is turned toward the pole of said metallic cotyle, whereas upper and opposite edges of the T are parallel with respect to one another.

19. The metallic cotyle according to claim 15, wherein the grooves each have a T-shaped profile whose upper and lower edges are inclined with respect to an axis, such that the largest end is turned toward the pole of said metallic cotyle.

20. The metallic cotyle according to claim 15, wherein the grooves open up toward the peripheral edge.

21. An acetabular or cotyloid implant comprising:
a plastic insert;
a metallic cotyle member including, a peripheral edge, an outer surface and an internal cavity adapted to receive the plastic insert;
grooves arranged on the outer surface;
each of the grooves being adapted to receive at least one independent element and comprising at least two non-parallel edges or surfaces; and
a distance between the at least two-non-parallel edges or surfaces being greater at a second end than at a first end of each of the grooves,
wherein the first end of each of the grooves is closer to the peripheral edge than the second end of each of the grooves, and
wherein the grooves are adapted to prevent ejection of the at least one independent element when the metallic cotyle member is inserted in a cavity.

22. The implant of claim 21, wherein the first end of each of the grooves is positioned at the peripheral edge.

23. The implant of claim 21, wherein each of the grooves has a conical profile and is adapted to receive various independent elements.

24. The implant of claim 21, wherein the outer surface of the metallic cotyle member comprises one of a curved or semi-spherical outer surface.

25. The implant of claim 21, wherein at least one of the grooves is T-shaped.

26. The implant of claim 21, wherein each of the grooves further comprises two oppositely facing parallel surfaces or edges.

27. The implant of claim 21, wherein the at least two non-parallel surfaces or edges comprises four oppositely facing non-parallel surfaces or edges.

28. The implant of claim 21, wherein each of the grooves extend to or from the peripheral edge such that each first end opens out to the peripheral edge.

29. The implant of claim 21, further comprising:
the outer surface being one of a curved or semi-spherical outer surface and a comprising a pole;
each of the grooves extending from the peripheral edge toward the pole; and
each of the grooves further comprising at least two opposite facing parallel surfaces or edges adapted to engage corresponding surfaces of the independent element.

30. The implant of claim 21, wherein each of the grooves comprises a shape which is one of T-shaped or dovetail shaped.

31. The implant of claim 30, wherein the outer surface is one of a curved or semi-spherical, and wherein each of the grooves opens out to the peripheral edge.

32. The implant of claim 31, wherein the internal cavity comprises two conical portions and a flat bottom portion, at least one of the conical portions or the flat bottom portion having at least one through hole.

33. The implant of claim 21, further comprising the at least one independent element having a tenon which engages at least one of the grooves.

34. The implant of claim 33, wherein the tenon has at least one inclined surface which engages a surface of the at least one of the grooves.

35. The implant of claim 34, wherein the at least one independent element further comprises another portion connected to the tenon, the other portion comprising one of a disc, a triangle-shaped piece, a half-sphere shell, a curved plate, and a rectilinear plate.

36. A metallic cotyle member for use in acetabular or cotyloid implant, the metallic cotyle member comprising:
an outer surface and a peripheral edge;
grooves arranged on the outer surface;
each of the grooves being adapted to receive at least one independent element and comprising at least two non-parallel edges or surfaces; and
a distance between the at least two-non-parallel edges or surfaces being greater at a second end than at a first end of each of the grooves,
wherein the first end of each of the grooves is closer to the peripheral edge than the second end of each of the grooves, and
wherein the grooves are adapted to prevent ejection of the at least one independent element when the metallic cotyle member is inserted in a cavity.

* * * * *